＝

US008785420B2

(12) United States Patent
Abou Chacra Vernet et al.

(10) Patent No.: US 8,785,420 B2
(45) Date of Patent: *Jul. 22, 2014

(54) COMBINATION/ASSOCIATION OF ADAPALENE AND BENZOYL PEROXIDE FOR TREATING ACNE LESIONS

(75) Inventors: Marie-Line Abou Chacra Vernet, Nice (FR); Denis Gross, Callian (FR); Christian Loesche, Valbonne (FR); Michel Poncet, Mougins (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/351,986

(22) Filed: Jan. 17, 2012

(65) Prior Publication Data

US 2012/0115947 A1 May 10, 2012

Related U.S. Application Data

(63) Continuation of application No. 11/826,364, filed on Jul. 13, 2007, now Pat. No. 8,129,362.

(60) Provisional application No. 60/833,491, filed on Jul. 27, 2006.

(30) Foreign Application Priority Data

Jul. 13, 2006 (FR) ...................... 06 52968

(51) Int. Cl.
*A61K 31/60* (2006.01)
*A61P 17/10* (2006.01)
*A61K 31/235* (2006.01)
*A61K 31/70* (2006.01)

(52) U.S. Cl.
USPC ............. 514/165; 514/544; 514/24; 514/859; 514/714

(58) Field of Classification Search
USPC ....................................... 514/544
See application file for complete search history.

(56) References Cited

U.S. PATENT DOCUMENTS

| | | | |
|---|---|---|---|
| 5,733,886 | A | 3/1998 | Baroody et al. |
| 6,559,189 | B2 * | 5/2003 | Baker et al. .................. 514/642 |
| 2003/0170196 | A1 | 9/2003 | Orsoni et al. |
| 2005/0148495 | A1 | 7/2005 | Lambert et al. |
| 2005/0239723 | A1 | 10/2005 | Amin et al. |
| 2006/0128808 | A1 | 6/2006 | Arsonnaud et al. |
| 2009/0191245 | A1 | 7/2009 | Fredon et al. |

FOREIGN PATENT DOCUMENTS

| | | |
|---|---|---|
| FR | 2 833 841 | 6/2003 |
| WO | 2006/045640 A1 | 5/2006 |
| WO | WO 2007/002831 A2 | 1/2007 |
| WO | 2007/132134 A1 | 11/2007 |

OTHER PUBLICATIONS (Wen-Wen et al., "Clinical efficacy and safety of 5% benzoyl peroxide gel combined with 0.1% adapalene gel in the treatment of acne vulgaris: a multicenter randomized study", Database Biosis, Biosciences Information Service, Jun. 2003, Database accession No. PREV200300514701, pp. 310-312, vol. 36, No. 6.*
Capizzi et al. ("Efficacy and Safety of Combination Therapy of Hydrogen Peroxide Cream and Adapalene Gel in Comparison with Benzoyl Peroxide Cream and Adapalene in Common Acne," Journal of the American Academy of Dermatology, vol. 50, Issue 3, Supplement 1, p. P18 (Mar. 2004)).*
Gollnick et al. (Evaluation of a maintenance treatment of acne vulgaris with adapalene gel, 0.1%. JEADV (2004) 18 (Suppl. 2), 193-557).*
Extended European Search Report issued on Mar. 30, 2012, in corresponding European Patent Application No. 12 15 2317, Written Opinion and originally filed claims 1-10 of EP 12 15 2317 (14 pages).
Daniele Caron Ph. D et al. "Skin Tolerance of Adapalene 0.1% Gel in Combination with other Topical Antiacne Treatments" *Journal of the American Academy of Dermatology* Jun. 1997 pp. S113-S115 vol. 36, No. 6.
B. Martin et al. "Chemical Stability of Adapalene and Tretinoin when Combined with Benzoyl Peroxide in Presence and in Absence of Visible Light and Ultraviolet Radiation" *British Journal of Dermatology* Oct. 1998 pp. 8-11 vol. 139 No. Suppl. 52.
C. Korkut et al. "Benzoyl Peroxide, Adapalene, and their Combination in the Treatment of Acne Vulgaris" *The Journal of Dermatology* 2005 vol. 32 No. 3 pp. 169-173.
Jonathan S. Weiss et al. "Adapalene for the Treatment of Acne Vulgaris" *Journal of the American Academy of Dermatology* Aug. 1998 vol. 39 No. 2 pp. S50-S54.
Gollnick et al. "Evaluation of a Maintenance Treatment of Acne Vulgaris with Adapalene Gel 0.1%" *Journal of the American Academy of Dermatology* Mar. 2005 p. 18 vol. 52 No. 3.
R. Capizzi et al. "Skin Tolerability and Efficacy of Combination Therapy with Hydrogen Peroxide Stabilized Cream and Adapalene Gel in Comparison with Benzoyl Peroxide Cream and Adapalene Gel in Common Acne. A Randomized, Investigator-Masked, Controlled Trial" *British Journal of Dermatology* 2004 vol. 151 No. 2 pp. 481-484.

(Continued)

Primary Examiner — Layla Soroush
(74) Attorney, Agent, or Firm — Dentons US LLP

(57) ABSTRACT

Acne lesions, whether of inflammatory and/or non-inflammatory type, are simultaneously or sequentially treated and their number reduced, via daily topical regimen, with the combination or association of adapalene or pharmaceutically acceptable salt thereof and benzoyl peroxide (BPO).

12 Claims, 5 Drawing Sheets

(56) References Cited

OTHER PUBLICATIONS

A. Clucas et al. "Adapalene 0.1% gel has Low Skin Irritation Potential" *Journal of the European Academy of Dermatology and Venereology*, Elsevier Science Publishers Sep. 1998 vol. 11, p. S275.
Joseph B. Bikowski "Clinical Experience Results with Clindamycin 1% Benzoyl Peroxide 5% Gel (Duac®) as Monotherapy and in Combination" *Journal of Drugs in Dermatology* Mar. 2005 vol. 4 No. 2 pp. 164-171.
Barbara Brand et al. "Cumulative Irritancy Comparison of Adapalene gel 0.1% Versus other Retinoid Products when Applied in Combination with Topical Antimicrobial Agents" *Journal of American Academy of Dermatology* Sep. 2003 vol. 49 No. 3 pp. S227-S232 Cranberry, NJ.
Wen-Wen et al. "Clinical Efficacy and Safety of 5% Benzoyl Peroxide Gel Combined with 0.1% Adapalene Gel in the Treatment of Acne Vulgaris: A Multicenter, Randomised Study" *Database Biosis (Online)* Jun. 2003 vol. 36 No. 6 pp. 310-312.
S. Hurwitz "The Combined Effect of Vitamin A Acid and Benzoyl Peroxide in the Treatment of Acne" *Cutis, Excerpta Medica* 1976 vol. 17 No. 3 pp. 585-590, New Haven, CT.
Leyden "A Review of the Use of Combination Therapies for the Treatment of Acne Vulgaris," *Journal of the American Academy of Dermatology*, vol. 49, No. 3, pp. S200-S210 (Sep. 2003).
International Search Report for corresponding PCT/EP2007/057207 dated Sep. 24, 2007.
Office Actions mailed Oct. 21, 2009 and Mar. 3, 2011 for U.S. Appl. No. 12/318,937, filed Jan. 13, 2009.
Office Action mailed Mar. 25, 2011 for U.S. Appl. No. 12/473,981, filed May 28, 2009.
LV do Nascimento et al., "Single-blind comparative clinical study of the efficacy and safety of benzoyl peroxide 4% gel (BID) and adapalene 0.1% Gel (QD) in the treatment of acne vulgaris for 11 weeks," Journal of Dermatological Treatment, 2003, pp. 166-171, vol. 14.
Official Action issued on Sep. 25, 2012, by the Japanese Patent Office in corresponding Japanese Patent Application No. 2009-518901, and an English language translation thereof (6 pages in Japanese and 6 pages in English) with an English language of the examined claims (3 pages).
Tan et al, "Synergistic efficacy of adapalene 0.1%-benzoyl peroxide 2.5% in the treatment of 3855 acne vulgaris patients", Journal of Dermatological Treatment, 2010, Early Online, pp. 1-9, Informa UK Ltd., UK.
Mills et al., "A human model for assaying comedolytic substances", British Journal of Dermatology, 1982, vol. 107, pp. 543-548, British Association of Dermatologists, UK.
Mills et al., "Assay of Comedolytic Activity in Acne Patients," Acta Derm. Venereol., 1983, 63(1), pp. 68-71, Stockholm.

\* cited by examiner

COMBINATION/ASSOCIATION OF ADAPALENE AND BENZOYL PEROXIDE FOR TREATING ACNE LESIONS

CROSS-REFERENCE TO EARLIER APPLICATIONS

This application is a continuation of earlier U.S. patent application Ser. No. 11/826,364, filed Jul. 13, 2007, now allowed, which claims benefit of U.S. Provisional Application No. 60/833,491, filed Jul. 27, 2006 and claims priority of FR 06/52968, filed Jul. 13, 2006, each hereby expressly incorporated by reference and each assigned to the assignee hereof.

BACKGROUND OF THE INVENTION

1. Technical Field of the Invention

The present invention relates to the combined or associated administration of adapalene and of benzoyl peroxide for reducing the number of acne lesions.

2. Description of Background and/or Related and/or Prior Art

6-[3-(1-Adamantyl)-4-methoxyphenyl]-2-naphthoic acid (referred to hereinbelow as adapalene) is a naphthoic acid derivative with retinoid and anti-inflammatory properties. This molecule was the subject of development for the topical treatment of common acne and of dermatoses sensitive to retinoids.

Adapalene is marketed under the trademark Differin® at a weight concentration of 0.1%, in the form of an "alcoholic lotion" solution, an aqueous gel and a cream. These compositions are useful for treating acne. FR-2,837,101 describes adapalene compositions at a weight concentration of 0.3%, for treating acne.

WO 03/055 472 moreover describes stable pharmaceutical compositions comprising adapalene and benzoyl peroxide (BPO).

An article by Korkut and Piskin, *J. Dermatology*, 2005, 32: 169-173, reports the results of a study comparing a treatment combining application of adapalene in the evening and application of BPO in the morning, relative to an application of each of the active principles alone. The authors do not observe any superiority of the combined treatment over a period of 11 weeks of treatment.

SUMMARY OF THE INVENTION

It has now surprisingly been demonstrated that a therapeutic association or combination of adapalene and BPO can produce a degree of success in reducing the number of acne lesions and an improvement in the clinical condition of patients that is markedly superior to a treatment based on adapalene alone or on BPO alone, while at the same time maintaining the same skin tolerance.

The recommended treatment may take the form of a pharmaceutical composition combining adapalene and BPO, or a concomitant application of two pharmaceutical compositions, one comprising adapalene and the other comprising BPO.

The present invention thus features formulation of adapalene or a pharmaceutically acceptable salt thereof for the preparation of a pharmaceutical composition, especially at set doses, suited to be administered in combination or in association with benzoyl peroxide (BPO), for the treatment of acne lesions, especially to reduce the number of acne lesions and to improve the clinical condition of patients.

Preferably, the acne lesions are of inflammatory and/or non-inflammatory type.

Acne is initially characterized by keratinization disorders, which are sometimes invisible to the naked eye. Visible acne lesions then develop, while the size of the sebaceous glands and the production of sebum increase.

The present invention specifically concerns acne lesions. The term "acne lesions" means non-inflammatory lesions (open and closed comedones) and inflammatory lesions (papules, pustules, nodules and cysts) caused by acne. Preferably, the inflammatory lesions are treated with the association or the combination according to the invention.

More preferably, the pharmaceutical composition is administered by daily cutaneous topical application. Stated differently, the invention relates to the use of adapalene as an agent for potentiating the action of BPO. Reciprocally, BPO potentiates the action of adapalene.

The term "adapalene salts" means the salts formed with a pharmaceutically acceptable base, especially mineral bases such as sodium hydroxide, potassium hydroxide and ammonia or organic bases such as lysine, arginine or N-methylglucamine. The term "adapalene salts" also means the salts formed with fatty amines such as dioctylamine and stearylamine.

The expression "combination of adapalene or salts thereof with benzoyl peroxide" means a single composition comprising both adapalene or salts thereof and benzoyl peroxide.

According to one preferred embodiment, the pharmaceutical composition is a fixed combination and comprises, in a pharmaceutically acceptable medium, (i) at least one compound selected from adapalene and pharmaceutically acceptable salts thereof, and (ii) benzoyl peroxide (BPO). Preferably, the pharmaceutical composition is intended for a single topical application per day.

The term "pharmaceutically acceptable medium" means a medium that is compatible with the skin, mucous membranes and the integuments.

The term "fixed combination" should be understood as meaning a combination whose active principles are combined at fixed doses in the same vehicle (single formula) that delivers them together to the point of application. Preferably, the pharmaceutical composition in the form of a fixed combination is a gel; in this case, the two active principles are dispersed and intimately mixed, during the manufacture, in the same vehicle, which delivers them together during the application of the gel.

In another embodiment of the invention, the pharmaceutical composition is in the form of a composition A comprising adapalene, intended to be applied concomitantly with a composition B comprising BPO. Preferably, composition A and composition B are presented in the form of a kit, preferably comprising two isolated compartments each containing one of the two pharmaceutical compositions A or B (dual pack) and allowing simultaneous administration of the two compositions, or alternatively in the form of a kit combining in the same presentation at least the two products (compositions A and B) in two separate packages, preferably in the form of tubes (co-packaging).

In this case, one skilled in the art will adapt the formula that is the most appropriate in terms of viscosity, additives, etc. to the selected kit.

The expression "concomitant" application means that the compositions are to be applied to the skin simultaneously or one after the other, in any order, or in a sequential order (for example, in which the application of a pharmaceutical composition B comprising BPO precedes the application of the pharmaceutical composition A comprising adapalene), but within a time interval of less than 1 hour, preferably less than 30 minutes, preferably less than 15 minutes, more preferably less than 5 minutes or even less than 1 minute.

The invention thus also features a composition in kit form comprising at least two components:

a first component comprising at least adapalene or a pharmaceutically acceptable salt thereof, a second component comprising benzoyl peroxide, these two components to be applied concomitantly to the skin, mucous membranes and/or the integuments.

Compositions A and B are preferably suited for a single cutaneous topical application per day.

The treatments have a variable duration, depending on the patient and the severity of his acne. The treatment period may thus run from several weeks to several months. A suitable treatment period or regimen is at least two weeks, preferably from 1 to 6 months and more preferably a duration of about 3 months is preferable, the duration of the treatment possibly being prolonged, if necessary.

Figure 1:
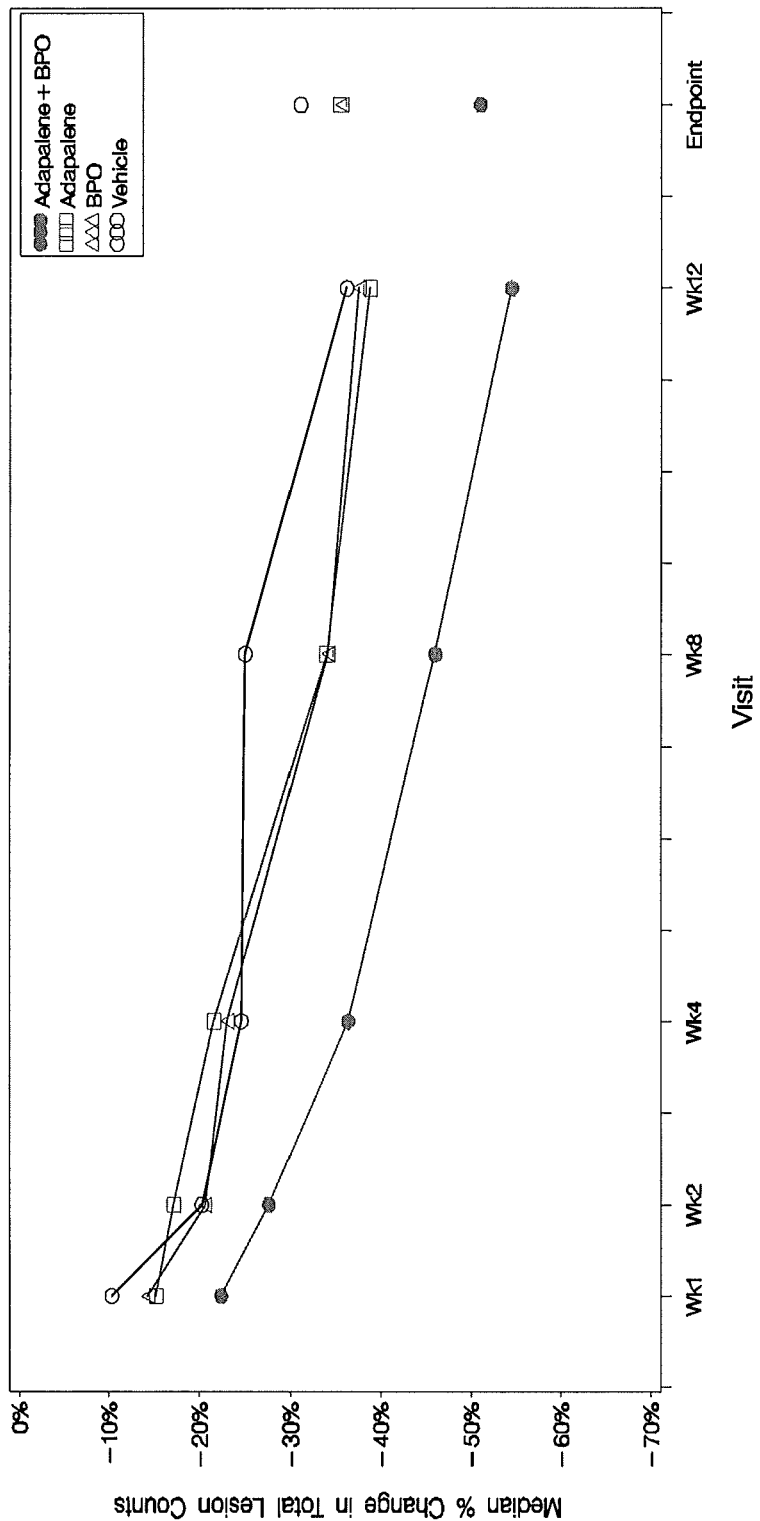
FIGS. 1-4 are graphs showing the efficacy of adapalene+BPO according to the invention versus adapalene alone, BPO alone and vehicle alone.
Figure 2:
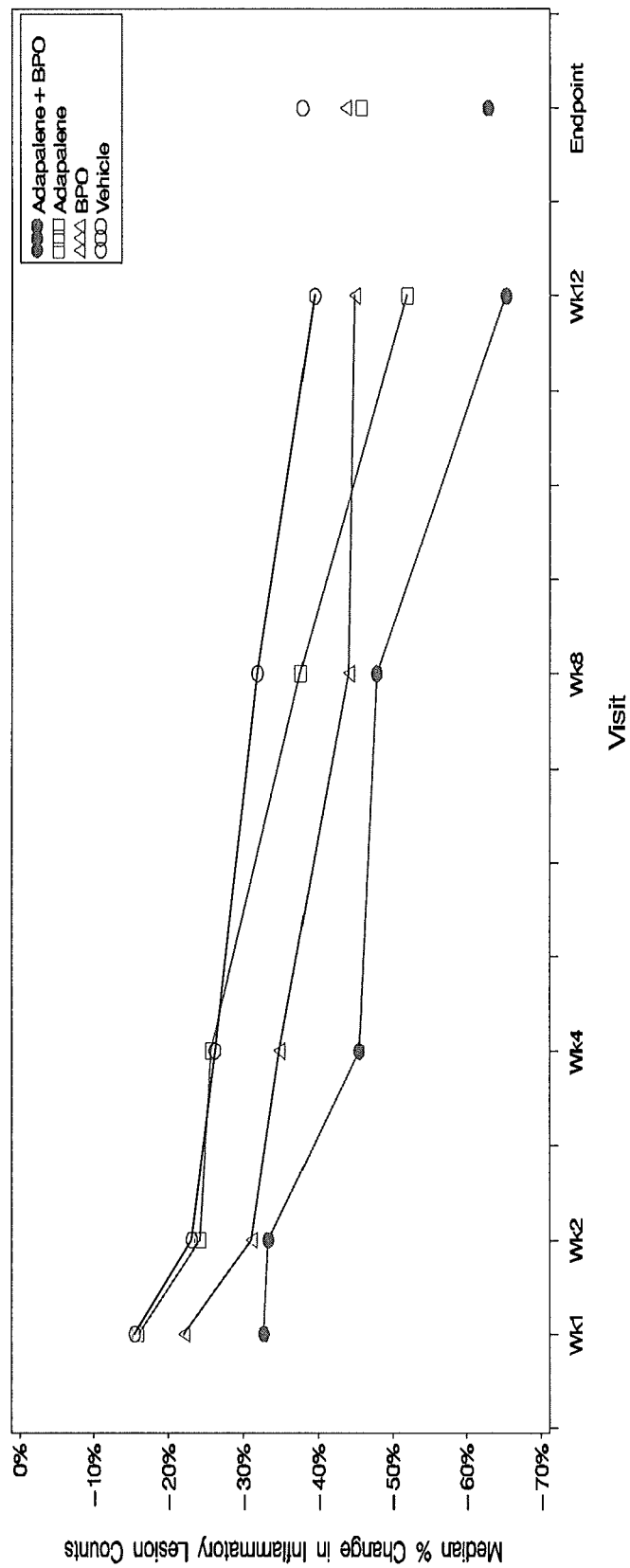
Figure 3:
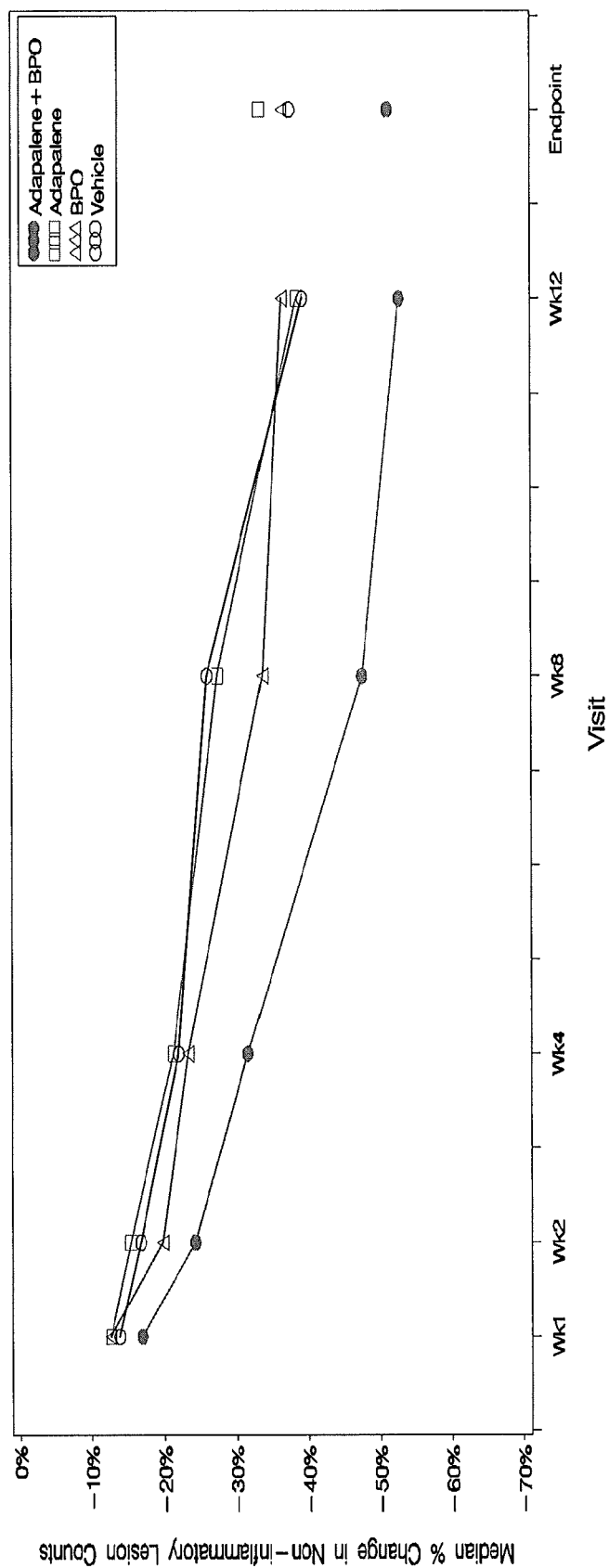
Figure 4:
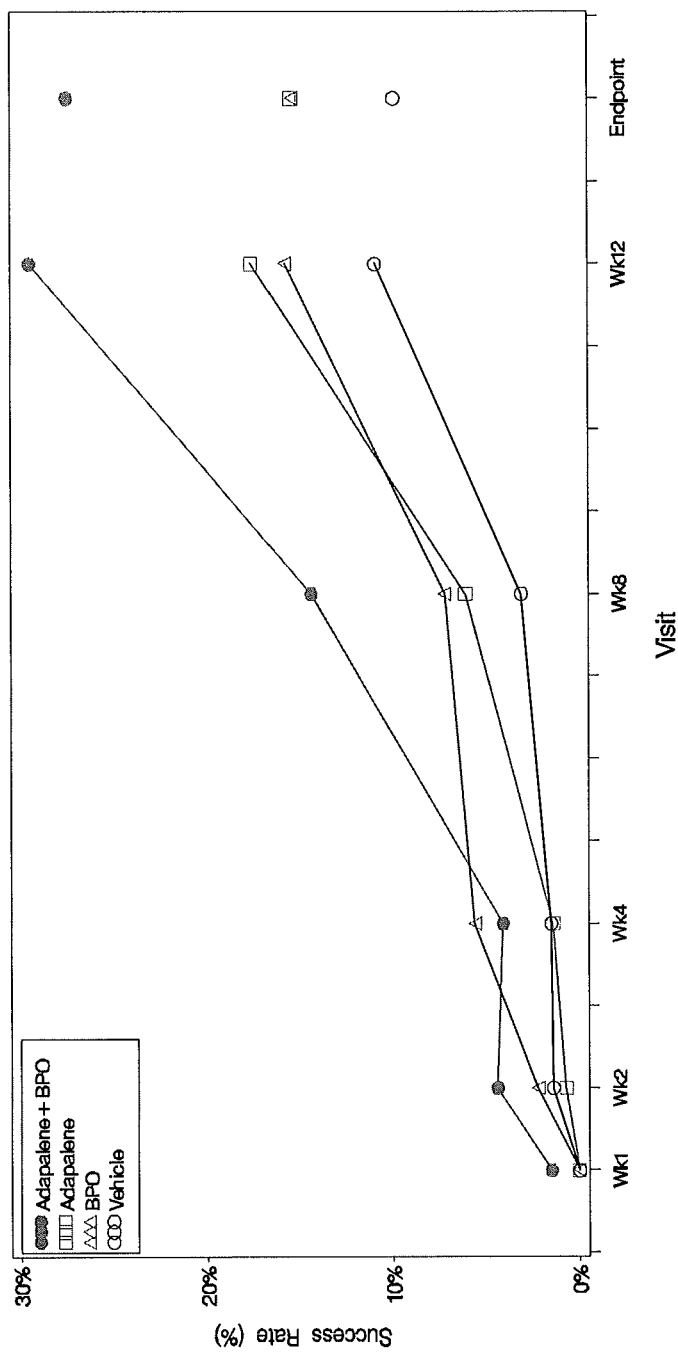

DETAILED DESCRIPTION OF BEST MODE AND SPECIFIC/PREFERRED EMBODIMENTS OF THE INVENTION

All the pharmaceutical compositions according to the invention may comprise from 0.01% to 2%, preferably from 0.05% to 0.5% and preferentially from 0.1% to 0.3% of adapalene, and from 0.1% to 20% and preferably from 0.5% to 10% of BPO, more preferably from 2% to 5% of BPO and preferentially 2.5% of BPO.

All the percentages are indicated by weight relative to the total weight of the composition.

The adapalene:BPO ratio is from 1:1 and 1:200 and, conversely, the BPO:adapalene ratio is from 1:1 and 1:200. Preferably, the adapalene:BPO ratio is from 1:1 and 1:200 and the adapalene:BPO ratio is preferably 1:25.

Preferably, the effect of the combination of the two active principles is at least an additive effect and preferentially a potentiation or synergistic effect. The terms "potentiation effect" and "synergistic effect" mean a therapeutic effect (degree of success) greater than the effect resulting from the addition of the effects obtained by each of the two active principles taken separately.

When they are combined in the same pharmaceutical composition, the adapalene and the BPO are present in the pharmaceutical composition in synergistic amounts, i.e., such that a synergistic or potentiation effect on the acne lesions and on the clinical condition of the patient is observed. Preferably, the pharmaceutical composition comprises 0.1% of adapalene and 2.5% of BPO.

When compositions A and B are used separately, the adapalene and the BPO are, respectively, present in composition A and composition B in synergistic amounts, i.e., such that a synergistic or potentiation effect on the acne lesions and on the clinical condition of the patient is observed, especially when the compositions are applied in association in equal amounts. Preferably, composition A comprises 0.1% of adapalene and composition B comprises 2.5% of BPO.

In this regard, the examples to follow demonstrate that due to the synergistic effect of adapalene and BPO, the invention provides greater efficacy for the treatment of acne in general and of acne lesions in particular and a quicker onset of action relative to monotherapies.

The pharmaceutical compositions according to the invention may be in the form of ointments, emulsions preferably in the form of creams, milks or pomades; powders, impregnated pads, solutions, gels, sprays, lotions or suspensions. They may also be in the form of suspensions of microspheres or nanospheres or of lipid or polymer vesicles or of polymer patches and/or of hydrogels allowing controlled release. These compositions may be in anhydrous form, in aqueous form or in the form of an emulsion.

In one preferred embodiment of the invention, the pharmaceutical compositions are in the form of a gel, a cream or a solution referred to as a lotion.

Preferably, the pharmaceutical compositions combining adapalene and BPO, or the pharmaceutical compositions A and/or B, are gels.

The pharmaceutical compositions according to the invention may contain inert additives or combinations of these additives, such as:

wetting agents;
texture enhancers;
preservatives such as para-hydroxybenzoic acid esters;
stabilizers;
humidity regulators;
pH regulators;
osmotic pressure modifiers;
emulsifiers;
UV-A and UV-B screening agents; and
antioxidants, such as a-tocopherol, butylhydroxyanisole or butylhydroxytoluene, superoxide dismutase, ubiquinol, or certain metal-chelating agents.

Needless to say, one skilled in this art will take care to select the optional compound(s) to be added to these compositions such that the advantageous properties intrinsically associated with the present invention are not, or are not substantially, adversely affected by the envisaged addition.

According to one particular embodiment, the pharmaceutical composition A comprising adapalene may be an aqueous gel especially containing one or more ingredients selected from the carbomer 940 (BF Goodrich Carbopol 980) and propylene glycol, or a cream especially containing one or more ingredients selected from perhydrosqualene, cyclomethicone, PEG-20 methylglucose sesquistearate and methylglucose sesquistearate or an "alcoholic lotion" solution based on polyethylene glycol.

Useful pharmaceutical compositions, comprising adapalene and BPO, are moreover described in WO 03/055 472. Examples of such compositions comprise, besides the active principles adapalene and BPO:

from 5% to 25% of water;
from 0 to 10%, preferably from 0 to 2% and preferably less than 0.5% of liquid wetting surfactant;
from 0 to 10% of pro-penetrating agent; and
an aqueous phase comprising a pH-independent gelling agent.

According to one preferred embodiment, the preferred pharmaceutical composition, comprising adapalene and BPO, is an aqueous gel having the following formulation:

2.5% of BPO;
0.1% of adapalene;
0.10% of disodium EDTA;
4.00% of glycerol;
4.00% of propylene glycol;

and also, preferably:
- 0.05% of sodium docusate;
- 0.20% of poloxamer 124;
- 4.00% of sodium acryloyldimethyltaurate copolymer and isohexadecane and polysorbate 80;
- NaOH, in an amount sufficient to obtain a pH of 5.

The acne targeted comprises all forms of acne, including common acne, comedones, polymorphs, nodulocystic acne, acne conglobata, and secondary acne such as solar, medicational or occupational acne. The acne may in particular be of mild to severe intensity and preferably of mild to moderate intensity. The compositions according to the invention may be administered as a firstline treatment, and also after failure of other specific treatments including the administration of adapalene and/or of BPO according to the conditions described by Korkut et al.

The association or combination of adapalene and of BPO makes it possible to reduce not only the number of inflammatory acne lesions but also the non-inflammatory acne lesions and to observe an improvement in the patient's clinical condition. A potentiation or synergistic effect is observed. This potentiation effect described in the example below is shown in the reduced number of lesions and in the percentage of cured patients (clear) and almost cured patients (almost clear) by the size of the superiority of the combination at fixed doses of adapalene and of BPO, relative to the active substances taken individually at the same doses as the combination.

Moreover, the results of the potentiation effect of the combination of adapalene and BPO presented in the example are statistically different from the results obtained for the active substances taken individually.

The combination or association of adapalene and of BPO is thus particularly useful for reducing the number of inflammatory and/or non-inflammatory acne lesions. Preferably, the reduction is at least about 40%, preferably at least about 50% and more preferably the reduction is at least about 60%. Similarly, it is demonstrated in the example that the reduction of the total lesions is from about 35% to 80% and preferably from about 50% to 70%.

According to another aspect, the invention also features a pharmaceutical assembly (product) comprising:
 i) a container delimiting at least one compartment, the said container being closed by means of a closing member; and
 ii) a pharmaceutical composition comprising adapalene or a pharmaceutically acceptable salt thereof and benzoyl peroxide as described above, and placed inside the said compartment.

The container may be in any suitable form. It may especially be in the form of a bottle, a tube, a jar, a case, a can, a sachet or a box.

Preferably, the container comprises two compartments, and each of these compartments comprises either composition A or composition B.

The closing member may be in the form of a removable stopper, a lid, a cover, a tear-off strip or a cap, especially of the type comprising a body fixed to the container and a cap articulated on the body. It may also be in the form of a member ensuring the selective closure of the container, especially a pump, a valve or a clapper.

The closing member may be coupled to the container by screwing. Alternatively, the coupling from the closing member and the container may take place other than by screwing, especially via a bayonet mechanism, by click-fastening, gripping, welding, bonding or magnetic attraction. The term "click-fastening" in particular means any system involving the passing of a rim or bead of material by elastic deformation of a portion, especially of the closing member, followed by return to the elastically unstressed position of the said portion after the rim or bead has been passed.

The container may be at least partly made of thermoplastic material. Examples of thermoplastic materials that are representative include polypropylene and polyethylene.

Alternatively, the container is made of a non-thermoplastic material, especially of glass or metal (or alloy).

The container may have rigid walls or deformable walls, especially in the form of a tube or a tube bottle.

The container may comprise means for causing or facilitating the distribution of the composition. By way of example, the container may have deformable walls so as to make the composition come out in response to a positive pressure inside the container, this positive pressure being caused by elastic (or non-elastic) squeezing of the walls of the container. Alternatively, especially when the product is in the form of a stick, this stick may be driven by a piston mechanism. Still in the case of a stick, especially of makeup product, the container may comprise a mechanism, especially a wishbone mechanism, or a mechanism with a threaded stem, or with a helical ramp, which is capable of moving a stick in the direction of the said opening. Such a mechanism is described, for example, in FR-2,806,273 or in FR-2,775,566. Such a mechanism for a liquid product is described in FR-2,727,609.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Clinical Study Results

A clinical study for confirmation of efficacy was performed for a topical gel combining adapalene+benzoyl peroxide (BPO).

This gel has the following formulation (expressed as % weight/total weight):

| | |
|---|---|
| Adapalene | 0.10% |
| Benzoyl peroxide | 2.50% |
| Copolymer of acrylamide & sodium acryloyldimethyltaurate | 4.00% |
| Sodium docusate | 0.05% |
| Disodium EDTA | 0.10% |
| Glycerol | 4.00% |
| Poloxamer 124 | 0.20% |
| Propylene glycol | 4.00% |
| Purified water | qs 100% |

Protocol:

The clinical study was a multi-centre, randomized, double-blind study in parallel groups, to evaluate the tolerance and the efficacy of the above formulation, in comparison with its own individual active substances placed at the same doses in gels of the same formula as that of the fixed combination (individual formulae referred to as "monads") and in comparison with the gel vehicle (placebo formula):adapalene gel (0.1%), BPO gel (2.5%) and vehicle gel.

All the treatments were applied once a day for 12 weeks, to 517 patients suffering from acne.

The main efficacy criteria were:

the degree of success, defined as the percentage of patients considered as being "clear", i.e., the patient has no more acne lesions (neither comedones nor inflammatory lesions), reflecting an improvement in the patient's clinical condition, or "almost clear" on the evaluation scale;

the reduction of the percentage of inflammatory and non-inflammatory lesions after 12 weeks of treatment.

Results:

The results are presented in the table that follows and in FIGS. 1-4.

| | Efficacy in week 12 ITT* | | | |
|---|---|---|---|---|
| | Adapalene 0.1% + BPO 2.5% N = 149 | Adapalene 0.1% alone N = 148 | BPO 2.5% alone N = 149 | Vehicle (gel) N = 71 |
| Degree of success (see FIG. 4) | 27.5% | 15.5% | 15.4% | 9.9% |
| Progress of the lesions (median percentages) | | | | |
| Number of inflammatory lesions (see FIG. 2) | −62.8% | −45.7% | −43.6% | −37.8% |
| Number of non-inflammatory lesions (see FIG. 3) | −51.2% | −33.3% | −36.4% | −37.5% |
| Total number of lesions (see FIG. 1) | −51.0% | −35.4% | −35.6% | −31.0% |
| Progress of the lesions (as median absolute numbers) | | | | |
| Number of inflammatory lesions | −17 | −13.0 | −13.0 | −11.0 |
| Number of non-inflammatory lesions | −22.0 | −17.0 | −16.0 | −14.0 |
| Total number of lesions | −40.0 | −29.0 | −27 | −26.0 |

ITT* (analysis of intention to treat): all the patients randomized in a clinical test because they come under the indication selected for the treatment to be prescribed. The missing data are imputed by the last observation (LOCF method ** (Last Observation Carried Forward).

For the 4 main criteria of the study: degree of success and progress as a percentage of the three types of lesion, the fixed combination was found to be statistically superior to the two monads and to the vehicle.

When the effect of the gel used as vehicle (V) is subtracted from the effect of the fixed combination (C), the net clinical benefit of the fixed combination (C−V) is numerically superior to the sum of the net clinical benefits of each of the individual substances after subtraction of the vehicle effect from the adapalene (A) and BPO (B) branches, respectively, according to the equation:

$$(C-V) > (A-V) + (B-V).$$

These results systematically show a potentiation effect since the net benefit is in favor of the gel combining adapalene+BPO, with results, in terms of degree of success, that are superior to the addition of adapalene and BPO (28% for the combination, as opposed to 16%, 15% and 10% for adapalene, BPO and vehicle, respectively). In this case, the above equation shows (28−10)>(16−10)+(15−10), i.e., 18>11, which is true.

Similarly, the gel combining adapalene+BPO was numerically superior in terms of efficacy in comparison with the individual active substances and with the vehicle as regards the reduction in the number of all the lesions (reduction in the percentage of inflammatory and non-inflammatory lesions).

A potentiation effect of adapalene and BPO together is thus noted, since a 51% reduction in lesions is observed for the combination, as opposed to 35% for adapalene alone, 36% for BPO alone and 31% for the vehicle, which is expressed as a net benefit of efficacy with the above equation by (51−31)>(35−31)+(36−31), i.e., 20>9, which is accurate.

Example 2

Evaluation of the Anti-Inflammatory in Ear Edema Model on Balb/c Mice

The study was carried out with 45 (5 par groups) female 9 weeks aged Balb/c ByJlc mice.

The Edema was induced by a single application of 20 µl of TPA dissolved in acetone at 0.01%.

The treatment was administrated by single topical application of tested compounds dissolved in TPA at 0.01% (groups 3, 4, 5, 6 and 7) and dissolved in TPA 0.01%+BPO (groups 8, 9 and 10).

The treatments activity was measured by inflammation evaluation with ear thickness at T+6 hours.

Figure 5:
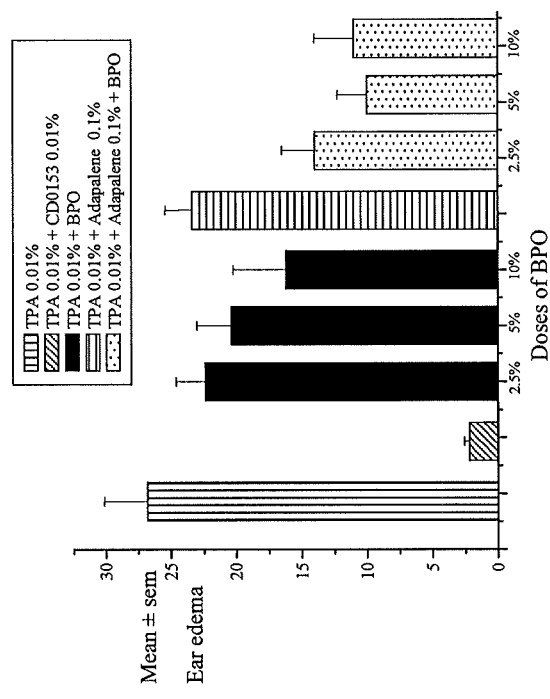
FIG. 5 is a bar graph showing the effects on ear edema of a variety of test compounds.

The results are presented in the following table and in FIG. 5.

| | Ear Edema Mean | sem | Inhibition vs TPA (%) | Repeated Annova Testing vs TPA alone (Dose Balanced) | Repeated Annova Testing vs TPA + BPO (Dose Balanced) |
|---|---|---|---|---|---|
| Acetone | | | | | |
| TPA 0.01% | 26.80 | 3.35 | | | |
| TPA 0.01% + CD153 0.01 (controle) | 2.20 | 0.37 | 91.8 | | |
| TPA 0.01% + BPO at 2.5% | 22.40 | 2.23 | 16.4 | 0.042 | |
| TPA 0.01% + BPO at 5% | 20.40 | 2.62 | 23.9 | | |
| TPA 0.01% + BPO at 10% | 16.20 | 4.03 | 39.6 | | |
| TPA 0.01% + Adapalene at 0.1% | 23.40 | 2.01 | 12.7 | | |
| TPA 0.01% + Adapalene at 0.1% + BPO at 2.5% | 14.00 | 2.51 | 47.8 | | |
| TPA 0.01% + Adapalene at 0.1% + BPO at 5% | 10.00 | 2.26 | 62.7 | | 0.0015 |
| TPA 0.01% + Adapalene at 0.1% + BPO at 10% | 11.00 | 3.03 | 59.0 | | |

CONCLUSION

After a single topical application of the positive control CD0153 (0.01%) diluted in TPA solution, a decrease of 92% of the ear thickness was observed.

BPO at 2.5%, 5% and 10% has a slight anti-inflammatory effect, reducing the TPA-induced ear edema respectively by 16%, 24% and 40%, with a statistically significant dose balanced effect (0.042).

Adapalene alone has a low anti-inflammatory effect, reducing the TPA-induced ear edema by 13%.

Variation of concentration of BPO was measured in combination with adapalene. Therefore, combinations of BPO at 2.5%, 5% and 10% with Adapalene at 0.1% reduce the TPA-induced ear edema respectively by 48%, 63% and 59%. Combination treatment is statistically more efficient than BPO alone (0.0015) even though the dose effect of the latest group is non-significant regarding the TPA alone group (0.1089).

Adapalene at 0.1% increase the anti-inflammatory effect obtained with BPO whatever tested doses.

Lower doses of BPO will be used to attempt to show a dose related effect for the association.

These results show a potential synergistic anti-inflammatory effect of the combination compared to the compounds singly applied.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regimen for the therapeutic treatment of acne lesions, the regimen comprising topically applying to the skin of a subject in need of said treatment, as active ingredients, 0.1% to 0.3% adapalene and 2.5% benzoyl peroxide, combined at fixed doses in a single formula that delivers said active ingredients together synergistically to achieve, in a group of such subjects, a degree of success of at least about 20%, wherein said single formula is applied once daily for a period of 12 weeks.

2. The regimen of claim 1, wherein the single formula is a gel.

3. A regimen for the therapeutic treatment of acne lesions, the regimen comprising topically applying to the skin of a subject in need of said treatment, as active ingredients, 0.1% to 0.3% adapalene and 2.5% benzoyl peroxide, combined at fixed doses in a single formula that delivers said active ingredients together synergistically to reduce the number of total acne lesions by at least 40%, wherein said single formula is applied once daily for a period of 12 weeks.

4. The regimen of claim 3, wherein the single formula is a gel.

5. A regimen for the therapeutic treatment of acne lesions, the regimen comprising topically applying to the skin of a subject in need of said treatment, as active ingredients, 0.1% to 0.3% adapalene and 2.5% benzoyl peroxide, combined at fixed doses in a single formula that delivers said active ingredients together synergistically to reduce the number of non-inflammatory acne lesions by at least 40%, wherein said single formula is a gel which is applied once daily for a period of 12 weeks.

6. A regimen for the therapeutic treatment of acne lesions, the regimen comprising topically applying to the skin of a subject in need of said treatment, as active ingredients, 0.1% to 0.3% adapalene and 2.5% benzoyl peroxide, combined at fixed doses in a single formula that delivers said active ingredients together synergistically to reduce the number of inflammatory acne lesions by at least 50%, wherein said single formula is a gel which is applied once daily for a period of 12 weeks.

7. A regimen for the therapeutic treatment of acne lesions, the regimen comprising topically applying to the skin of a subject in need of such treatment, as active ingredients, 0.1% to 0.3% adapalene and 2.5% benzoyl peroxide, combined at fixed doses in a single formula that delivers said active ingredients together synergistically to reduce the number of inflammatory lesions by at least 40%, wherein said single formula is applied once daily for a period of 12 weeks.

8. The regimen of claim 7, wherein the single formula is a gel.

9. A regimen for the therapeutic treatment of acne lesions, the regimen comprising topically applying to the skin of a subject in need of said treatment, as active ingredients, 0.1% to 0.3% adapalene and 2.5% benzoyl peroxide, combined at fixed doses in a single formula that delivers said active ingredients together synergistically to reduce the number of total acne lesions by at least 40%, to reduce the number of non-inflammatory acne lesions by at least 40%, to reduce the number of inflammatory acne lesions by at least 40% and to achieve in a group of such subjects, a degree of success of at least about 20%, wherein said single formula is applied once daily for a period of 12 weeks.

10. The regimen of claim 9, wherein the single formula is a gel.

11. A regimen for providing early onset of action in reducing total lesion counts in the therapeutic treatment of acne lesions, the regimen comprising topically applying to the skin of a subject in need of said treatment, as active ingredients, 0.1% to 0.3% adapalene and 2.5% benzoyl peroxide, combined at fixed doses in a single formula that delivers said active ingredients together, wherein said single formula is applied once daily for a period of 1, 2, or 4 weeks, and wherein the net reduction in total lesion counts in a group of such subjects, at week 1, week 2 or week 4, respectively, is numerically superior to the sum of the net reductions in total lesion counts achieved by the same dose of adapalene alone and of benzoyl peroxide alone at the corresponding time point.

12. The regimen of claim 11, wherein the single formula is a gel.

* * * * *